United States Patent
Nakada et al.

(12)

(10) Patent No.: US 6,190,651 B1
(45) Date of Patent: Feb. 20, 2001

(54) SOLUTION FOR PRESERVING CONTACT LENSES FOR SHIPPING AND METHOD FOR PRESERVING CONTACT LENSES FOR SHIPPING EMPLOYING IT

(75) Inventors: Kazuhiko Nakada, Aichi; Yutaka Matano, Gifu, both of (JP)

(73) Assignee: Menicon Co., Ltd., Nagoya (JP)

( * ) Notice: Under 35 U.S.C. 154(b), the term of this patent shall be extended for 0 days.

(21) Appl. No.: 09/353,795

(22) Filed: Jul. 15, 1999

(30) Foreign Application Priority Data

Aug. 3, 1998 (JP) .................................................. 10-218991

(51) Int. Cl.[7] .................................................. A67K 31/79
(52) U.S. Cl. ........................................ 424/78.24; 514/912
(58) Field of Search .......................... 424/78.24; 514/912

(56) References Cited

U.S. PATENT DOCUMENTS

| 4,560,491 | 12/1985 | Sherman . | |
|---|---|---|---|
| 4,836,986 | * 6/1989 | Ogunbiyi et al. | 422/28 |
| 5,300,296 | 4/1994 | Holly et al. . | |
| 5,453,435 | * 9/1995 | Raheja et al. | 514/402 |

FOREIGN PATENT DOCUMENTS

| 30 07 397 | 9/1981 | (DE) . |
|---|---|---|
| 0 526 654 | 2/1993 | (EP) . |

\* cited by examiner

*Primary Examiner*—Zohreh Fay
(74) *Attorney, Agent, or Firm*—Oblon, Spivak, McClelland, Maier & Neustadt, P.C.

(57) ABSTRACT

A solution for preserving contact lenses for shipping, which comprises a polyvinyl pyrrolidone having a weight average molecular weight of from 500 to 200,000, and which contains no surfactant.

10 Claims, No Drawings

SOLUTION FOR PRESERVING CONTACT LENSES FOR SHIPPING AND METHOD FOR PRESERVING CONTACT LENSES FOR SHIPPING EMPLOYING IT

The present invention relates to a solution for preserving contact lenses for shipping and a method for preserving contact lenses for shipping employing it.

Most of conventional contact lenses, particularly oxygen-permeable hard contact lenses contain silicon components. Accordingly, the surface of the contact lenses tends to be hydrophobic, and wettability is poor when they are firstly worn, whereby comfortableness in wearing tends to be poor, or satisfactory vision is less likely to be obtained. Accordingly, to keep the surface water wettability of said oxygen-permeable hard contact lenses, after they are produced until they are worn by patients, they are preserved as wet for shipping, by e.g. subjecting them to a surface treatment, or preliminarily immersing them in a preserving solution for shipping such as physiological saline.

However, in the case where contact lenses are preserved as wet for shipping by using e.g. physiological saline, there is a possibility that the base curve which is one of important specifications of contact lenses may change during the process for shipping.

Further, a surfactant is usually incorporated to many of conventional preserving solutions for shipping. Accordingly, a change in size of a contact lens such as the change in the base curve is likely to take place.

Under these circumstances, the present invention has been made, and it is an object of the present invention to provide a solution for preserving contact lenses for shipping, which significantly reduces a change in the base curve while contact lenses, particularly oxygen-permeable contact lenses, are preserved as wet for shipping, and a method for preserving contact lenses for shipping employing it.

The present invention relates to (1) a solution for preserving contact lenses for shipping, which comprises a polyvinyl pyrrolidone having a weight average molecular weight of from 500 to 200,000, and which contains no surfactant; (2) a solution for preserving contact lenses for shipping, which comprises from 0.2 to 3 w/v % of a polyvinyl pyrrolidone having a weight average molecular weight of from 500 to 200,000 and a K value of from 20 to 100, from 0.000005 to 0.0002 w/v % of a polyhexamethylene biguanide and from 0.02 to 0.3 w/v % of ethylenediaminetetraacetic acid, sodium ethylenediaminetetraacetate, or a hydrate of sodium ethylenediaminetetraacetate, and which contains no surfactant; and (3) a method for preserving contact lenses for shipping, which comprises immersing contact lenses in the above-mentioned solution (1) or (2).

Now, the present invention will be described in detail with reference to the preferred embodiments.

As mentioned above, the solution for preserving contact lenses for shipping of the present invention comprises a polyvinyl pyrrolidone having a weight average molecular weight of from 500 to 200,000, and contains no surfactant.

For the solution for preserving contact lenses for shipping of the present invention, a polyvinyl pyrrolidone is employed as an effective component to reduce the change in the base curve of a contact lens while the lens is preserved as wet for shipping.

The weight average molecular weight of the polyvinyl pyrrolidone is at least 500, preferably at least 1,000, considering that a certain level of molecular weight is required to obtain an adequate effect of stabilizing the base curve. Further, it is at most 200,000, preferably at most 150,000, considering a possibility that the solubility in a medium such as water will decrease, whereby an uniform solution for preserving contact lenses for shipping is less likely to be obtained, and considering a problem in handling efficiency due to increase in the viscosity.

The K value of the polyvinyl pyrrolidone as described in Japan Pharmacopoeia is at least 20, preferably at least 25, to obtain an adequate effect of stabilizing the base curve of a contact lens. Further, it is at most 100, preferably at most 90, considering a possibility that the solubility in a medium such as water will decrease, whereby an uniform solution for preserving contact lenses for shipping is less likely to be obtained, and considering a problem in handling efficiency due to increase in the viscosity. As a polyvinyl pyrrolidone having a K value of such a range, polyvinyl pyrrolidone K25, polyvinyl pyrrolidone K30 or polyvinyl pyrrolidone K90 may, for example, be mentioned.

The amount of the polyvinyl pyrrolidone in the solution for preserving contact lenses for shipping is at least 0.1 w/v %, preferably at least 0.2 w/v %, to obtain an adequate effect of reducing the change in the base curve of a contact lens while it is preserved as wet for shipping, by employing said polyvinyl pyrrolidone. Further, it is at most 10 w/v %, preferably at most 3 w/v %, to eliminate a possibility that the viscosity of the solution for preserving contact lenses for shipping will increase too much, whereby such a problem in handling may result that the contact lens is likely to get dirty as dried.

The solution for preserving contact lenses for shipping of the present invention preferably contains e.g. a preservative or a chelating agent in addition to the above-mentioned polyvinyl pyrrolidone.

The preservative serves to prevent contamination of the solution for preserving contact lenses for shipping by bacteria, and to prevent contamination of a contact lens during preservation for shipping.

The preservative is not particularly limited so long as it is ophthalmologically acceptable. It may, for example, be a compound which contains at least one member selected from the group consisting of a quaternary ammonium group, a biguanide group and a quaternary phosphonium group. Representative examples of said compound and other examples include a compound such as a polymer (I) having repeating units of the formula (I):

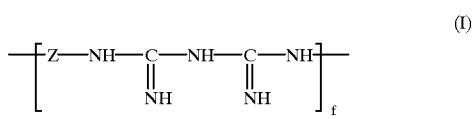
(I)

wherein Z is a bivalent organic group such as a $C_{2-18}$ polyoxyalkylene group, and f is an integer of at least 3, provided that the plurality of Z may be the same or different in the polymer, a polymer (II) having repeating units of the formula (II):

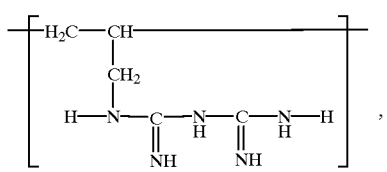
(II)

a polymer (III) having repeating units of the formula (III):

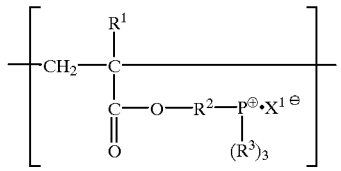
(III)

wherein $R^1$ is a hydrogen atom or a methyl group, $R^2$ is a $C_{1-8}$ alkylene group, $R^3$ is a $C_{1-18}$ alkyl group, and $X^1$ is a halogen atom such as a chlorine atom, a bromine atom or an iodine atom, and a polymer (IV) having repeating units of the formula (IV):

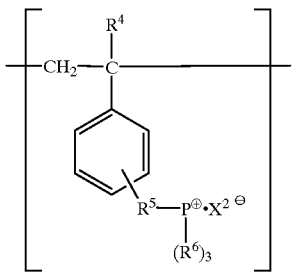
(IV)

wherein $R^4$ is a hydrogen atom or a methyl group, $R^5$ is a $C_{1-8}$ alkylene group, $R^6$ is a $C_{1-18}$ alkyl group, and $X^2$ is a halogen atom such as a chlorine atom, a bromine atom or an iodine atom, a mercury type preservative such as phenylmercury nitrate, phenylmercury acetate and thimerosal; a surfactant type preservative such as benzalkonium chloride and pyridinium bromide; an alcohol type preservative such as chlorohexyzine, polyhexamethylene biguanide and chlorobutanol; methylparaben, propylparaben, dimethylol dimethylhydantoin, imidazolinium urea; and a copolymer of e.g. a monomer (V) of the formula (V):

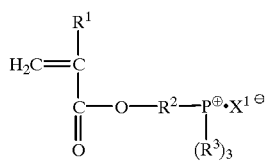
(V)

wherein $R^1$ is a hydrogen atom or a methyl group, $R^2$ is a $C_{1-8}$ alkylene group, $R^3$ is a $C_{1-18}$ alkyl group, and $X^1$ is a halogen atom such as a chlorine atom, a bromine atom or an iodine atom, or a monomer (VI) of the formula (VI):

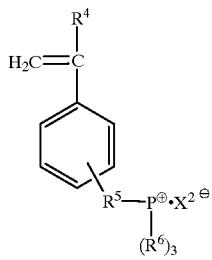
(VI)

wherein $R^4$ is a hydrogen atom or a methyl group, $R^5$ is a $C_{1-8}$ alkylene group, $R^6$ is a $C_{1-18}$ alkyl group, and $X^2$ is a halogen atom such as a chlorine atom, a bromine atom or an iodine atom, with a water-soluble monomer of e.g. a hydroxyalkyl(meth)acrylate such as hydroxymethyl(meth)acrylate, hydroxyethyl(meth)acrylate, hydroxypropyl(meth)acrylate or hydroxybutyl(meth)acrylate.

Further, various types of biguanide derivatives are commercially available, and in the present invention, the preservative may be suitably selected from these commercially available biguanide derivatives.

In view of a higher effect of preventing contamination by bacteria, such being effective, among the above-mentioned preservatives, at least one compound selected from the group consisting of the polymer (I), the polymer (II), the polymer (III) and the polymer (IV), the polyhexamethylene biguanide and the copolymer of the monomer (V) or the monomer (VI) with the water-soluble monomer, are particularly preferred.

The amount of the above-mentioned preservative in the solution for preserving contact lenses for shipping is at least 0.000005 w/v % (0.05 ppm), preferably at least 0.00005 w/v % (0.5 ppm), to obtain an adequate effect by its use. If the amount of such a preservative is too much, there will be a possibility that when the preservative is directly in contact with an eye, it may impair the eye, and depending upon the type, it may deteriorate the specifications or characteristics of contact lenses. Accordingly, the amount of the preservative is at most 0.5 w/v % (5,000 ppm), preferably at most 0.0005 w/v % (5 ppm), more preferably at most 0.0002 w/v % (2 ppm).

The above-mentioned chelating agent serves to prevent deposition of e.g. calcium in the solution for preserving contact lenses for shipping or in the tear on a contact lens.

The chelating agent is not particularly limited so long as it is opthalomologically acceptable, and examples of which include ethylenediaminetetraacetic acid, an ethylenediaminetetraacetate such as a sodium salt, and a hydrate of said ethylenediaminetetraacetate; phytic acid and citric acid. Among these, in view of a higher effect of preventing deposition of calcium, such being effective, ethylenediaminetetraacetic acid, an ethylenediaminetetraacetate and a hydrate of ethylenediaminetetraacetate are particularly preferred.

The amount of the above-mentioned chelating agent in the solution for preserving contact lenses for shipping is at least 0.01 w/v %, preferably at least 0.02 w/v %, to obtain an adequate effect of preventing deposition of e.g. calcium on a contact lens. Further, it is at most 0.5 w/v %, preferably at most 0.3 w/v %, since if the amount of the chelating agent is too much, the improvement in the effect of incorporating it is small, and such is uneconomical.

In the solution for preserving contact lenses for shipping of the present invention, a compounding agent such as a buffering agent or an isotonic agent may be contained in addition to the above-mentioned preservative and chelating agent.

The above-mentioned buffering agent serves to adjust the pH of the obtained solution for preserving contact lenses for shipping to be constant within a range of from about 5 to about 9 which is close to the tear, and to control the change in the pH due to external factors to protect the shape and the optical property of a contact lens during preservation for shipping.

The buffering agent is not particularly limited so long as it is opthalomologically acceptable, and examples of which include boric acid and its sodium salt, phosphoric acid and its sodium salt, citric acid and its sodium salt, lactic acid and its sodium salt, an amino acid such as glycine or glutamic acid and its sodium salt, and malic acid and its sodium salt.

The amount of the above-mentioned buffering agent in the solution for preserving contact lenses for shipping is at least 0.005 mol/l, preferably at least 0.01 mol/l, to obtain an adequate buffering effect. Further, it is at most 0.5 mol/l, preferably at most 0.15 mol/l, since if the amount of the buffering agent is too much, the buffering effect no longer increases, and the osmotic pressure may be increased so that it tends to influence the form of a contact lens.

The isotonic agent serves to bring the osmotic pressure of the obtained solution for preserving contact lenses for shipping close to the osmotic pressure of the tear (from 280 to 300 mOs/kg) so that the form of a contact lens is likely to be maintained during preservation for shipping.

The isotonic agent is not particularly limited so long as it is opthalomologically acceptable, and examples of which include an inorganic salt such as sodium chloride, potassium chloride or calcium chloride and the above-mentioned buffering agent.

The amount of the above-mentioned isotonic agent in the solution for preserving contact lenses for shipping is at least 0.01 mol/l, preferably at least 0.05 mol/l, to obtain an adequate osmotic pressure. Further, it is at most 0.5 mol/l, preferably at most 0.15 mol/l, since if the amount of the isotonic agent is too much, the osmotic pressure may be increased so that the form of a contact lens tends to be influenced.

The preservatives, the chelating agents, the buffering agents and the isotonic agents may be used alone or in combination as a mixture of two or more of them, respectively.

As mentioned above, the solution for preserving contact lenses for shipping comprises, as an effective component, a polyvinyl pyrrolidone having a specific weight average molecular weight, and contains components such as a preservative, a chelating agent and other compounding agent, as the case requires. As a medium, water such as distilled water or purified water may be incorporated thereto. Such an aqueous medium as said water may be used to bring the total of the solution for preserving contact lenses for shipping to 100%.

The solution for preserving contact lenses for shipping of the present invention is prepared, for example, in such a manner that the polyvinyl pyrrolidone is added into a predetermined amount of an aqueous medium, and as the case requires, a compounding agent such as a preservative, a chelating agent, a buffering agent or an isotonic agent is added thereto, and they are adequately mixed by stirring for dissolution, followed by filtration.

The viscosity of the solution for preserving contact lenses for shipping of the present invention is not particularly limited. However, it is preferably at a level of not higher than 200 cP at 25° C., taking handling efficiency for preserving contact lenses for shipping into consideration.

The pH of the solution for preserving contact lenses for shipping is preferably from 5 to 9 which is the same level of the tear, more preferably from 6.6 to 7.6, considering a case where the solution for preserving contact lenses for shipping is in contact with an eye, even though there is little possibility that it is in directly contact with the eye.

As the solution for preserving contact lenses for shipping of the present invention, a preserving solution for shipping, which comprises from 0.2 to 3 w/v % of a polyvinyl pyrrolidone having a weight average molecular weight of from 500 to 200,000 and a K value of from 20 to 100, from 0.000005 to 0.0002 w/v % (from 0.05 to 2 ppm) of a polyhexamethylene biguanide and from 0.02 to 0.3 w/v % of ethylenediaminetetraacetic acid, sodium ethylenediaminetetraacetate, or a hydrate of sodium ethylenediaminetetraacetate, and which contains no surfactant, is particularly preferred, as a higher effect of reducing the change in the base curve can be obtained when a contact lens is preserved as wet for shipping.

Various contact lenses can be preserved for shipping with little change in the base curve, by immersing the contact lenses into the solution for preserving contact lenses for shipping of the present invention thus obtained.

In the method for preserving contact lenses for shipping of the present invention, for example, a contact lens and the solution for preserving contact lenses for shipping in an amount such that said contact lens is thoroughly immersed therein, are put in a predetermined container, and closed.

The method for preserving contact lenses for shipping of the present invention may be applied on any contact lens regardless of the type such as water-absorptive type, non water-absorptive type, soft type or hard type. Even with an oxygen-permeable hard contact lens obtained by polymerization of a siloxanyl(meth)acrylate type monomer, a siloxanylstyrene type monomer or a polymerizable component containing a silicone compound such as siloxanyl fumarate or siloxanyl itaconate, the change in the base curve is significantly reduced during preservation as wet for shipping.

Now, the solution for preserving contact lenses for shipping of the present invention and the method for preserving contact lenses for shipping employing it will be described in further detail with reference to Examples. However, it should be understood that the present invention is by no means restricted to such specific Examples.

EXAMPLE 1

Polyvinyl pyrrolidone K30 (weight average molecular weight: 45,000, K value: 30), a polyhexamethylene biguanide and trisodium ethylenediaminetetraacetate.2H$_2$O were added to distilled water, followed by stirring at room temperature for about 60 minutes to dissolve these components, and the solution was subjected to filtration to prepare 300 ml of a solution for preserving contact lenses for shipping. The amounts of these components are as follows:

Polyvinyl pyrrolidone K30: 1.0 w/v %

Polyhexamethylene biguanide: 1.0 ppm

Trisodium ethylenediaminetetraacetate.2H$_2$O: 0.10 w/v %

EXAMPLE 2

The same operation as in Example 1 was carried out except that polyvinyl pyrrolidone K90 (weight average molecular weight: 110,000, K value: 90) was used instead of polyvinyl pyrrolidone K30, the amount of said polyvinyl pyrrolidone K90 was 0.5 w/v %, and the amount of the polyhexamethylene biguanide was 0.5 ppm, to prepare 300 ml of a solution for preserving contact lenses for shipping.

With respect to the solutions for preserving contact lenses for shipping obtained in Examples 1 and 2, solubility, appearance, smell, pH and viscosity were tested in accordance with the following methods. The results are shown in Table 1.

(1) Solubility

Each solution for preserving contact lenses for shipping was visually observed, and the solubility was evaluated on the basis of the following evaluation standards indicating presence or absence of impurities in the solution.

Evaluation Standards

A: No impurity was observed.
B: Impurities were slightly observed.
C: Impurities were significantly observed.

(2) Appearance

The appearance of each solution for preserving contact lenses for shipping was visually observed and evaluated on the basis of the following evaluation standards.

Evaluation Standards

A: The solution was uniform and transparent.
B: The solution was slightly cloudy.
C: The solution was significantly cloudy.

(3) Smell

The smell of the solution for preserving contact lenses for shipping was observed from a distance of 5 cm, and evaluated on the basis of the following evaluation standards.

Evaluation Standards

A: No smell was observed.
B: Smell was slightly observed.
C: Smell was significantly observed.

(4) pH

The pH of the solution for preserving contact lenses for shipping was measured by a glass electrode type pH meter (HORIBA pH METER F-13, manufactured by HORIBA) at 25° C.

(5) Viscosity

The viscosity (cP) of the solution for preserving contact lenses for shipping was measured by a B type viscometer at 25° C.

Then, a polymerizable component comprising 50 parts by weight of siloxanyl methacrylate, 40 parts by weight of trifluoroethyl methacrylate, 10 parts by weight of methylmethacrylate and 5 parts by weight of ethylene glycol dimethacrylate was copolymerized followed by shaping, to produce oxygen-permeable hard contact lenses having a thickness of 0.12 mm.

5 Sheets of the oxygen-permeable hard contact lenses were prepared for each of the solutions for preserving contact lenses for shipping obtained in Examples 1 and 2, and the base curves were preliminarily measured.

Then, the oxygen-permeable hard contact lenses and the solution for preserving contact lenses for shipping were put in a contact lens case for shipping, the oxygen-permeable hard contact lenses were immersed in the solution for preserving contact lenses for shipping, and the case was closed and preserved at 40° C. After 2 weeks and 4 weeks, respective base curves were measured.

Changes in base curves were obtained from the difference between the base curve after the preservation and the base curve measured preliminarily, the average change of 5 sheets of contact lenses was calculated, and the rate of change in base curve (%) was obtained from the average base curve of 5 sheets of the contact lenses, on the basis of the following formula. The results are shown in Table 1.

Rate of change in base curve (%)={(average change in base curve)/(average of base curves before the preservation)}×100

Comparative Example 1

Using physiological saline instead of the solution for preserving contact lenses for shipping in Example 1 or 2, the rate of change in base curve was obtained in the same manner as in Example 1 or 2. The results are shown in Table 1.

TABLE 1

| | Properties of solution for preserving contact lenses for shipping | | | | | Rate of change in base curve (%) | |
|---|---|---|---|---|---|---|---|
| | Solubility | Appearance | Smell | pH | Viscosity (cP) | After 2 weeks | After 4 weeks |
| Example 1 | A | A | A | 7.0 | 50≧ | 0.1 | 0.1 |
| Example 2 | A | A | A | 7.0 | 50≧ | 0.1 | 0.1 |
| Comparative Example 1 | — | — | — | — | — | 0.4 | 0.8 |

As evident from the results shown in Table 1, the solutions for preserving contact lenses for shipping obtained in Examples 1 and 2, have an appropriate pH and viscosity, are excellent in solubility and appearance, and are free from smell.

Further, when contact lenses are preserved by using the solutions for preserving contact lenses for shipping obtained in Examples 1 and 2, the rate of change in base curve of the contact lenses is significantly small after the preservation of 2 weeks, and even after the preservation of 4 weeks, as compared with Comparative Example 1 wherein physiological saline was used.

The solution for preserving contact lenses for shipping of the present invention is excellent in solubility and appearance, and is free from smell. When contact lenses, particularly oxygen-permeable hard contact lenses, are preserved as wet for shipping by using the solution for preserving contact lenses for shipping, a change in the base curve which is one of important specifications of contact lenses can be significantly reduced.

What is claimed is:

1. A method for preserving contact lenses for shipping, which comprises storing contact lenses in a solution containing a polyvinyl pyrrolidone having a weight average molecular weight of from 500 to 200,000, and a K value of from 20 to 100, and which contains no surfactant.

2. The method for preserving contact lenses for shipping according to claim 1, which contains a preservative.

3. The method for preserving contact lenses for shipping according to claim 2, wherein the preservative is a compound which contains at least one member selected from the group consisting of a quaternary ammonium group, a biguanide group and a quaternary phosphonium group.

4. The method for preserving contact lenses for shipping according to claim 2, wherein the preservative is at least one compound selected from the group consisting of a polymer (I) having repeating units of the formula (I):

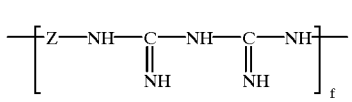

(I)

wherein Z is a bivalent organic group, and f is an integer of at least 3, provided that the plurality of Z may be the same or different in the polymer; a polymer (II) having repeating units of the formula (II):

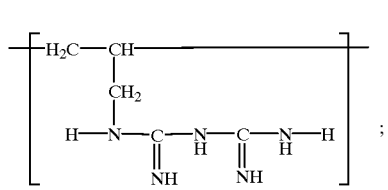

(II)

a polymer (III) having repeating units of the formula (III):

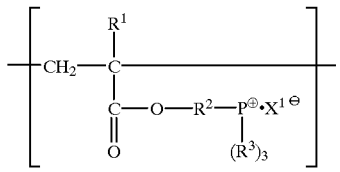

(III)

wherein $R^1$ is a hydrogen atom or a methyl group, $R^2$ is a $C_{1-8}$ alkylene group, $R^3$ is a $C_{1-18}$ alkyl group, and $X^1$ is a halogen atom; and a polymer (IV) having repeating units of the formula (IV):

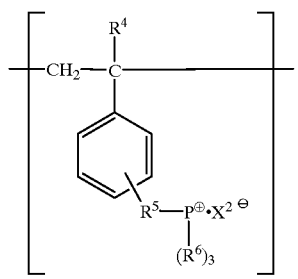

(IV)

wherein $R^4$ is a hydrogen atom or a methyl group, $R^5$ is a $C_{1-8}$ alkylene group, $R^6$ is a $C_{1-18}$ alkyl group, and $X^2$ is a halogen atom.

5. The method for preserving contact lenses for shipping according to claim 2, wherein the preservative is a polyhexamethylene biguanide, or a copolymer of a monomer (V) of the formula (V):

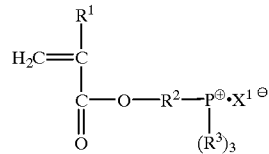

(V)

wherein $R^1$ is a hydrogen atom or a methyl group, $R^2$ is a $C_{1-8}$ alkylene group, $R^3$ is a $C_{1-18}$ alkyl group, and $X^1$ is a halogen atom, or a monomer (VI) of the formula (VI):

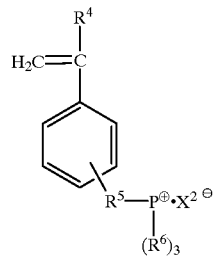

(VI)

wherein $R^4$ is a hydrogen atom or a methyl group, $R^5$ is a $C_{1-8}$ alkylene group, $R^6$ is a $C_{1-18}$ alkyl group, and $X^2$ is a halogen atom, with a water-soluble monomer.

6. The method for preserving contact lenses for shipping according to claim 1, which contains a chelating agent.

7. The method for preserving contact lenses for shipping according to claim 6, wherein the chelating agent is ethylenediaminetetraacetic acid, an ethylenediaminetetraacetate, or a hydrate of the ethylenediaminetetraacetate.

8. The method for preserving contact lenses for shipping according to claim 1, which has a pH of from 6.6 to 7.6.

9. A method for preserving contact lenses for shipping, which comprises from 0.2 to 3 w/v % of a polyvinyl pyrrolidone having a weight average molecular weight of from 500 to 200,000 and a K value of from 20 to 100, from 0.000005 to 0.0002 w/v % of a polyhexamethylene biguanide and from 0.02 to 0.3 w/v % of ethylenediaminetetraacetic acid, sodium ethylenediaminetetraacetate, or a hydrate of sodium ethylenediaminetetraacetate, and which contains no surfactant.

10. The method for preserving contact lenses for shipping according to claim 9, which has a pH of from 6.6 to 7.6.

* * * * *